(12) United States Patent
Nagasawa et al.

(10) Patent No.: US 8,404,710 B2
(45) Date of Patent: *Mar. 26, 2013

(54) PHOSPHODIESTERASE 10A INHIBITOR

(75) Inventors: Michiaki Nagasawa, Tochigi (JP); Simon John Mackenzie, Strathclyde (GB)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 272 days.

This patent is subject to a terminal disclaimer.

(21) Appl. No.: 12/913,094

(22) Filed: Oct. 27, 2010

(65) Prior Publication Data

US 2011/0039882 A1  Feb. 17, 2011

Related U.S. Application Data

(63) Continuation of application No. 11/980,526, filed on Oct. 31, 2007, now Pat. No. 7,846,942, which is a continuation of application No. 10/537,313, filed as application No. PCT/JP03/15315 on Dec. 1, 2003, now abandoned.

(30) Foreign Application Priority Data

Dec. 3, 2002 (JP) .................. 2002-350804

(51) Int. Cl.
  *A61K 31/437* (2006.01)
  *A61P 25/16* (2006.01)
(52) U.S. Cl. .................................................. 514/300
(58) Field of Classification Search .................. 546/121; 514/300

See application file for complete search history.

(56) References Cited

U.S. PATENT DOCUMENTS

| | | | |
|---|---|---|---|
| 6,265,577 B1 | 7/2001 | Kouno et al. | |
| 7,846,942 B2 * | 12/2010 | Nagasawa et al. | 514/300 |
| 2008/0108650 A1 | 5/2008 | Nagasawa et al. | |

FOREIGN PATENT DOCUMENTS

| | | |
|---|---|---|
| JP | 2-131424 | 5/1990 |
| JP | 11-302190 | 11/1999 |
| JP | 2000-224992 | 8/2000 |
| WO | 00/09127 | 2/2000 |
| WO | 01/24781 | 4/2001 |
| WO | 01/40226 | 6/2001 |

OTHER PUBLICATIONS

Weishaar et al., Journal of medicinal chemistry, (May 1985), vol. 28, No. 5, pp. 537-545. Ref: 102.*
International Search Report issued Feb. 17, 2004 in International Application PCT/JP03/15315.
"Inhibitory Effect of Ibudilast (KC-404) on Cyclic Nucreotide Phosphodiesterases", Seiko Murashima: Mie Prefectural College of Nursing, et al., (Jpn Pharmacol Ther) vol. 26, No. 1 (1998), 41-45.
"Possible role of cyclic AMP phosphodiesterases in the actions of ibudilast on eosinophil thromboxane generation and airways smooth muscle tone" John E. Souness et al., Br.J. Pharmacol. (1994) 111, 1081-1088.
"Ibudilast Modulates Platelet-Endothelium Interaction Mainly Through Cyclic GMP-Dependent Mechanism", Journal of Cardiovascular Pharmacology 36(1) pp. 65-70 (2000), Kishi, Y. et al.
"Drug for improvement of Brain Circulation and Metabolism, and How to Use It", Hirotoshi Kasahara, et al., Clinica, 1990, 17 (5), pp. 256-262.
Reimund et al., Biochemical and biophysical research communications, vol. 288, pp. 427-434, 2001.
Souness et al., Biochemical pharmacology, vol. 58, pp. 991-999, 1999.
Suzumura et al., Brain Research, vol. 837, pp. 203-212, 1999.
Kishi et al., Journal of cardiovascular pharmacology, vol. 36, pp. 65-70, 2000.
Supplementary European Search Report of Aug. 21, 2008 issued in connection with the European application corresponding to the present US application.
Iwasaki K. et al., "Ibudilast Improved the Memory Disturbances and Hippocampal Apoptosis in Now—Transgenic Animal Model of Alzheimer's Disease," Society for Neuroscience Abstract Viewer and Itinerary Planner, vol. 2002; Abstract No. 685.6, XP002492918, 2002.
The Merck Manual (Japanese Edition): 17th Edition, Mark H. Beers et al. 1999, pp. 1400-1405.
Weishaar et al., Journal of Medicinal Chemistry, vol. 28, No. 5, pp. 537-545, May 1985.
K. Loughney et al., "Isolation and characterization of PDE10A, a novel human 3', 5'-cyclic nucleotide phosphodiesterase", Gene 234, 1999, pp. 109-117.
Kotomi Fujishige et al., "Cloning and Characterization of a Novel Human Phosphodiesterase That Hydrolyzes Both cAMP and cGMP (PDE10A)", The Journal of Biological Chemistry, vol. 274, No. 26, 1999, pp. 18438-18445.

* cited by examiner

*Primary Examiner* — Niloofar Rahmani
(74) *Attorney, Agent, or Firm* — Wenderoth, Lind & Ponack, L.L.P.

(57) ABSTRACT

A phosphodiesterase 10A inhibitor serving as an effective prophylactic or therapeutic agent for Parkinson's disease, Huntington's disease, Alzheimer's disease, and schizophrenia.
The PDE10A inhibitor contains as an active ingredient a pyrazolo[1,5-a]pyridine derivative represented by the following general formula:

(1)

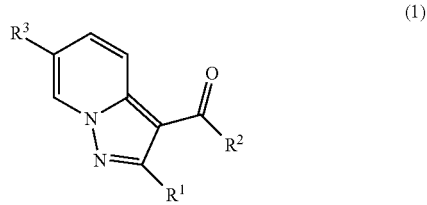

wherein $R^1$ and $R^2$ are each independently a hydrogen atom or a lower alkyl group having 1 to 4 carbons; and $R^3$ is a hydrogen atom, a lower alkyl group having 1 to 4 carbons, or a lower alkoxyl group having 1 to 3 carbons.

4 Claims, No Drawings

PHOSPHODIESTERASE 10A INHIBITOR

CROSS-REFERENCE TO RELATED APPLICATIONS

This application is a continuation of application Ser. No. 11/980,526, filed Oct. 31, 2007, now U.S. Pat. No. 7,846,942, which is a continuation of application Ser. No. 10/537,313, filed Sep. 28, 2005, now abandoned, which is a 371 application of PCT/JP2003/015315, filed Dec. 1, 2003.

TECHNICAL FIELD

The present invention relates to a phosphodiesterase 10A inhibitor containing a pyrazolo[1,5-a]pyridine derivative as an active ingredient. The present invention also relates to therapeutic agents for treating Parkinson's disease, Huntington's disease, Alzheimer's disease, and schizophrenia that contain the phosphodiesterase 10A inhibitor as an active ingredient.

BACKGROUND ART

[Patent Article 1] Japanese Patent Laid-Open Publication No. 2001-161379
[Patent Article 2] Japanese Patent Laid-Open Publication No. 2000-224992
[Patent Article 3] Pamphlet of International Patent Application No. WO 01/24781
[Patent Article 4] Japanese Patent Laid-Open Publication No. Sho 52-134870
[Patent Article 5] Japanese Patent Laid-Open Publication No. Hei 2-131424
[Non-patent Article 1] Fujishige et al., J. Biol. Chem., 274: 18438-45, 1999.
[Non-patent Article 2] Scott et al., Proc. Natl. Acad. Sci. USA, 96:7071-6. 1999; Fujishige et al., Eur. J. Biochem., 266:1118-27, 1999.
[Non-patent Article 3] Fujimoto et al., J. Neuroimmunol., 95:35-42, 1999.
[Non-patent Article 4] Souness et al., Brit. J. Pjarmacol., 11:1081-8, 1994; Murashima et al., Jpn. Pharmacol. Ther., 26:41-5, 1998; Kishi et al., J. Cardiovasc. Pharmacol., 36:65-70, 2000.

Phosphodiesterase (which may be referred to simply as PDE, hereinafter) is an enzyme that degrades cyclic AMP (cAMP) and cyclic GMP (cGMP), which play a significant role in various reactions in cells. In response to various extracellular signals, cAMP and cGMP are generated from ATP and GTP by the action of adenylyl cyclase and guanylyl cyclase and are degraded by PDE into 5'-AMP and 5'-GMP, respectively. Eleven different families of PDE have been identified so far. Each family specifically degrades cAMP, cGMP or both and has a different tissue distribution. It is thus believed that different types of PDE control cellular reactions in different organs.

Among many PDE inhibitors that have thus far been put to practical application are those inhibiting PDE3 (treatment for heart failure), PDE4 (treatment for asthma and COPD) and PDE5 (treatment for male erectile dysfunction).

In 1999, the presence of PDE10A, a new subtype of PDE, was reported in humans, mice, and rats. PDE10A is involved in the regulation of intracellular cAMP and cGMP levels and, in humans, exists predominantly in brain, testis, and thyroid. In brain, PDE10A is predominantly expressed in putamen and caudate nucleus that form neostriatum (Non-patent Article 1). High level expression of PDE10A is observed in brain and testis of mice and rats (Non-patent Article 2).

Human PDE10A gene was isolated and was evaluated for the susceptibility to different PDE inhibitors. The results indicated that PDE10A was inhibited by dipyridamole (Patent Article 1 and Patent Article 2). No specific examples were presented of application of the compound to actual disorders.

Only one example was reported, in which minocycline was used in the patients with Huntington's disease as a PDE10A modulator with positive results (Patent Article 3).

Pyrazolo[1,5-a]pyridine derivatives as represented by the general formula (1) below are known (Patent Article 4). Of these derivatives, 3-isobutyryl-2-isopropyl pyrazolo[1,5-a] pyridine, commonly known as ibudilast, is widely used as a cerebral circulation improver or a treatment for bronchial asthma and allergic conjunctivitis. Known effects of ibudilast include enhancement of the relaxation effect of prostacyclin (PGI2) on cerebral vascular smooth muscle, enhancement of the inhibitory effect of prostacyclin (PG12) on platelet aggregation, suppression of airway contraction, suppression of leukotriene release and inhibition of PDE, as well as improvement of memory disorder (Patent Article 5) and amelioration of multiple sclerosis (Non-patent Article 3).

Although ibudilast has been described to inhibit PDE3, PDE4, and PDE5 (Non-patent Article 4), nothing has been known about its activity as a PDE10 inhibitor.

DISCLOSURE OF THE INVENTION

The aim of the present invention is to provide a PDE10A inhibitor, which is a potential prophylactic or therapeutic agent against Parkinson's disease, Huntington's disease, Alzheimer's disease or, schizophrenia.

In the course of our search for a potential cure for diseases such as Parkinson's disease, Huntington's disease, Alzheimer's disease, and schizophrenia, the present inventors have discovered that some of the compounds with pyrazolopyridine structure have an activity to inhibit PDE10A. This discovery ultimately led to the present invention.

Specifically, the present invention concerns a phosphodiesterase 10A inhibitor that contains as an active ingredient a pyrazolo[1,5-a]pyridine derivative represented by the following general formula (1):

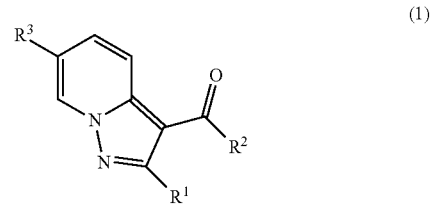

wherein $R^1$ and $R^2$ are each independently a hydrogen atom or a lower alkyl group having 1 to 4 carbons; and $R^3$ is a hydrogen atom, a lower alkyl group having 1 to 4 carbons, or a lower alkoxyl group having 1 to 3 carbons. The present invention also concerns a therapeutic agent for treating Parkinson's disease, Huntington's disease, Alzheimer's disease, and schizophrenia that contains the above-described phosphodiesterase 10A inhibitor.

BEST MODE FOR CARRYING OUT THE INVENTION

The present invention will now be described in detail.

Pyrazolo[1,5-a]pyridine derivatives as represented by the general formula (1) above are known compounds. Of these derivatives, 3-isobutyryl-2-isopropyl pyrazolo[1,5-a]pyridine, commonly known as ibudilast, is widely used as a cerebral circulation improver or a treatment for bronchial asthma and allergic conjunctivitis.

In the general formula (1), the lower alkyl group having 1 to 4 carbons may be methyl, ethyl, propyl, isopropyl, butyl, sec-butyl, or tert-butyl and is preferably isopropyl. The lower alkoxyl group having 1 to 3 carbons may be methoxy, ethoxy, propoxy, or isopropoxy.

When examined for the ability to inhibit different PDEs using cAMP and cGMP as a substrate, the compound of the present invention represented by the general formula (1) showed the strongest inhibition against PDE10A.

Parkinson's disease is known to be caused by a decreased supply of dopamine to neostriatum. It is believed that dopamine regulates the cAMP level in neostriatum (putamen and caudate nucleus) via D1 and D2 dopamine receptors present in the neostriatum. Since PDE10A is present specifically in these regions, an inhibitor of the enzyme is expected to have a potential as a novel treatment for Parkinson's disease.

Huntington's disease is characterized by the degeneration and shrinkage of neostriatum and its causative gene includes an abnormal extension of CAG repeats, suggesting inhibition of CREB-dependent transcription, an essential process in the survival of cells. Thus, a PDE10A inhibitor, which acts to increase the cAMP level in neostriatum, is expected to have a potential as a novel treatment for Huntington's disease.

Alzheimer's disease is a cerebral degenerative disease that leads to severe dementia and is characterized by deposition of beta-amyloids in nerve cells, degeneration of neurofibrils, loss of nerve cells and abnormal decrease of acetylcholine and other neurotransmitters. cGMP is known to facilitate the release of certain neurotransmitters, such as glutamic acid and acerylcholine, facilitate the growth of dendrites, increase the viability of nerve cells, and suppress apoptosis of nerve cells induced by beta-amyloids. Thus, by increasing brain cGMP level, Alzheimer's disease and other cerebral degenerative disorders may be ameliorated. Therefore, a PDE10A inhibitor, which may cause an increase in the brain cGMP level, is expected to have a potential as a novel treatment for Alzheimer's disease.

A major cause of schizophrenia is believed to be an imbalance of signaling mediated by neurotransmitters, glutamic acid, serotonin, and dopamine. The most plausible hypothesis for the cause of schizophrenia seems to be excessive release of dopamine in neostriatum. cGMP is known as a second messenger that facilitates the release of glutamic acid in neostriatum, so that an elevated cGMP level may modulate the balance of signaling mediated by neurotransmitters in neostriatum. Therefore, a PDE10A inhibitor, which may cause an increase in the cGMP level in neostriatum, is expected to have a potential as a novel treatment for schizophrenia.

For the reasons described above, the pyrazolo[1,5-a]pyridine derivatives represented by the general formula (1), which have proven to be effective PDE10A inhibitors, are thought to be effective in the prevention and treatment of Parkinson's disease, Huntington's disease, Alzheimer's disease, and schizophrenia.

Example

The present invention will now be described in detail with reference to examples, which are not intended to limit the scope of the invention in any way.

Example

Inhibition of PDEs by Ibudilast

1) Method cDNA of full length PDEs, specifically, PDE1A3, PDE2A3, PDE3A, PDE3B, PDE4A4, PDE4B2, PDE4C2, PDE4D3, PDE5A1, PDE5A2, PDE5A3, PDE7A2, PDE8A1, PDE9A2, PDE10A1, and PDE11A1, were isolated by RT-PCR from human RNA. The isolated cDNA fragments were introduced into Sf9 insect cells using Gateway system (Invitrogen) and Bac-to-Bac® Baculovirus Expression system (Invitrogen) to express PDE proteins. The recombinant proteins of PDE1A3, PDE2A3, PDE3A, PDE4A4, PDE4B2, PDE4C2, PDE4D3, PDE5A1, PDE5A2, PDE5A3, PDE7A2, PDE8A1, PDE9A2, PDE10A1, and PDE11A1 were purified by ion exchange chromatography from the supernatants or cell extracts of the Sf9 cells. For the recombinant PDE3B, the Sf9 cells expressing PDE3B protein at a high level were suspended in a RIPA buffer [150 mM NaCl, 10 mM Tris-HCl (pH8.3), 0.1% protease inhibitor cocktail (Product No.: P8849, Sigma)], and the whole suspension was used in the experiment described below.

A 4 mM solution of ibudilast was serially diluted 4-fold with a 15% DMSO solution to form ibudilast solutions of 15 nM to 4 mM (Final ibudilast concentrations used in the experiment were 1.5 nM to 400 µM). 10 µl of each ibudilast solution, 50 µl of a [$^3$H]cAMP or [$^3$H]cGMP solution (diluted with a buffer (40 mM Tris-HCl (pH7.4), 10 mM MgCl$_2$) to a concentration shown in Table 1), and 4 0 µl of each of the recombinant human PDE proteins (in units shown in Table 1) were added to a 96-well plate and the mixtures were incubated at 30° C. for 20 min and then at 65° C. for 2 min, 25 µl of 1 mg/ml 5'-nucleotidase (Crotalus atrox venom, Sigma) was then added to each well and the reactions were carried out at 30° C. for 10 min. Upon completion of the reaction, 200 µl Dowex solution (300 mg/ml Dowex 1x8-400 (Sigma Aldrich), 33% Ethanol) was added and the mixtures were agitated at 4° C. for 20 min. 200 µl MicroScint20 (Packard) was then added and the mixtures were analyzed by a scintillation counter (Topcount, Packard). IC50 values were determined by GraphPad Prism v.3.03 (GraphPad Software). The results are shown in Table 2.

TABLE 1

| Enzyme (amount) | Substrate | Conc. substrate |
| --- | --- | --- |
| PDE 1A3 (2 × 10$^{-6}$ units*) | cAMP | 2 µM |
| PDE 1A3 (2 × 10$^{-6}$ units) | cGMP | 2 µM |
| PDE 2A3 (2 × 10$^{-6}$ units) | cAMP | 2 µM |
| PDE 3 (All) (2 × 10$^{-6}$ units) | cAMP | 2 µM |
| PDE 4 (All) (2 × 10$^{-6}$ units) | cAMP | 2 µM |
| PDE 5 (All) (2 × 10$^{-6}$ units) | cGMP | 2 µM |
| PDE 7A2 (2 × 10$^{-7}$ units) | cAMP | 0.2 µM |
| PDE 8A1 (2 × 10$^{-7}$ units) | cAMP | 0.2 µM |
| PDE 9A2 (2 × 10$^{-7}$ units) | cGMP | 0.2 µM |
| PDE 10A1 (2 × 10$^{-7}$ units) | cAMP | 0.2 µM |
| PDE 10A1 (2 × 10$^{-6}$ units) | cGMP | 2 µM |
| PDE 11A1 (2 × 10$^{-6}$ units) | cAMP | 2 µM |
| PDE 11A1 (2 × 10$^{-7}$ units) | cGMP | 0.2 µM |

*1 unit of PDE corresponds to an amount of the enzyme that hydrolyzes 1 µM cAMP or cGMP at 30° C. and pH 7.5 in one minute.

2) Results

As shown in Table 2, the in vitro experiment using recombinant human PDE demonstrated that ibudilast had a particularly strong inhibition of PDE10A1.

TABLE 2

| PDE | Substrate | IC50 (μM) |
|---|---|---|
| PDE 1A3 | cAMP | 40 |
| PDE 1A3 | cGMP | 121 |
| PDE 2A3 | cAMP | 78 |
| PDE 3A | cAMP | 124 |
| PDE 3B | cAMP | 266 |
| PDE 4A4 | cAMP | 6 |
| PDE 4B2 | cAMP | 6 |
| PDE 4C2 | cAMP | 11 |
| PDE 4D3 | cAMP | 6 |
| PDE 5A1 | cGMP | >400 |
| PDE 5A2 | cGMP | 88 |
| PDE 5A3 | cGMP | 127 |
| PDE 7A2 | cAMP | 115 |
| PDE 8A1 | cAMP | 49 |
| PDE 9A2 | cGMP | >400 |
| PDE 10A1 | cAMP | 3 |
| PDE 10A1 | cGMP | 1 |
| PDE 11A1 | cAMP | 17 |
| PDE 11A1 | cGMP | 36 |

INDUSTRIAL APPLICABILITY

As set forth, pyrazolo[1,5-a]pyridine derivatives represented by the general formula (1) have proven to be strong inhibitors of PDE10A and have thus proven to be useful in the prevention and treatment of Parkinson's disease, Huntington's disease, Alzheimer's disease, and schizophrenia.

The invention claimed is:

1. A method of treating Parkinson's disease in a patient, which comprises administering to a patient in need thereof a therapeutically effective amount of a pyrazolo[1,5-a]pyridine derivative represented by the following general formula (I):

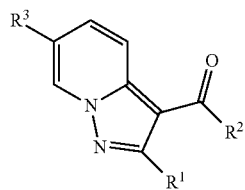

(1)

wherein $R^1$ and $R^2$ are each independently a hydrogen atom or a lower alkyl group having 1 to 4 carbons; and $R^3$ is a hydrogen atom, a lower alkyl group having 1 to 4 carbons, or a lower alkoxyl group having 1 to 3 carbons.

2. The method according to claim 1, wherein the compound represented by the general formula (1) is 3-isobutyryl-2-isopropyl pyrazolo[1,5-a]pyridine.

3. A method of treating Huntington's disease in a patient, which comprises administering to a patient in need thereof a therapeutically effective amount of a pyrazolo[1,5-a]pyridine derivative represented by the following general formula (I):

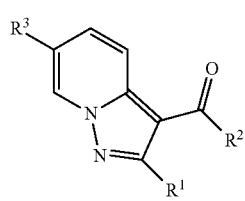

(1)

wherein $R^1$ and $R^2$ are each independently a hydrogen atom or a lower alkyl group having 1 to 4 carbons; and $R^3$ is a hydrogen atom, a lower alkyl group having 1 to 4 carbons, or a lower alkoxyl group having 1 to 3 carbons.

4. The method according to claim 3, wherein the compound represented by the general formula (1) is 3-isobutyryl-2-isopropyl pyrazolo[1,5-a]pyridine.

* * * * *